(12) United States Patent
Shaapur et al.

(10) Patent No.: US 6,188,068 B1
(45) Date of Patent: Feb. 13, 2001

(54) METHODS OF EXAMINING A SPECIMEN AND OF PREPARING A SPECIMEN FOR TRANSMISSION MICROSCOPIC EXAMINATION

(76) Inventors: Frederick F. Shaapur, 8096 E. Maria Dr., Scottsdale, AZ (US) 85255; Roger J. Graham, 2141 E. Euclid Ave., Phoenix, AZ (US) 85040

(*) Notice: Under 35 U.S.C. 154(b), the term of this patent shall be extended for 0 days.

(21) Appl. No.: 09/095,313

(22) Filed: Jun. 10, 1998

Related U.S. Application Data

(60) Provisional application No. 60/050,019, filed on Jun. 16, 1997.

(51) Int. Cl.[7] ................................................ G01N 1/28
(52) U.S. Cl. ...................... 250/307; 250/311; 250/492.2
(58) Field of Search .................................. 250/307, 311, 250/492.2

(56) References Cited

U.S. PATENT DOCUMENTS 5,656,811 * 8/1997 Itoh et al. ............................ 250/309
5,990,478 * 11/1999 Liu ..................................... 250/307

OTHER PUBLICATIONS

Novel Scheme For The Preparation of Transmission . . . Overwiijk et al. 1993.

Applications of Focused Ion Beams in Microelectronics . . . Stevie et al. 1995.

* cited by examiner

Primary Examiner—Teresa M. Arroyo
Assistant Examiner—Nikita Wells
(74) Attorney, Agent, or Firm—Parsons & Goltry; Michael W. Goltry; Robert A. Parsons

(57) ABSTRACT

A method of examining a specimen comprising the steps of providing transmission electron microscope apparatus, mounting a specimen in a vacuum chamber of focused ion beam apparatus, isolating a site of the specimen with the focused ion beam apparatus in the vacuum chamber, and with the site located in the vacuum chamber, examining the site with the transmission electron microscope apparatus.

16 Claims, 9 Drawing Sheets

METHODS OF EXAMINING A SPECIMEN AND OF PREPARING A SPECIMEN FOR TRANSMISSION MICROSCOPIC EXAMINATION

This application claims the benefit of U.S. Provisional Application Serial No. 60/050,019, filed Jun. 16, 1997.

FIELD OF THE INVENTION

This invention relates generally to sample preparation and examination methods and, more particularly, to methods of examining a specimen and of preparing a specimen for transmission electron microscope examination.

BACKGROUND OF THE INVENTION

Use of focused ion beam (FIB)-based techniques to prepare a sample from a specimen for transmission electron microscope (TEM) study or examination is popular and well known. The high lateral resolution of FIB in material removal normally allows removal of sample material at a selected site with sub-micron precision to form ultra-thin transverse sections for study or examination. Standard procedures normally include preparing a 20–50$\mu$m thick sample of specimen material by sawing, grinding and polishing, and thinning the sample to electron transparency using FIB techniques to produce a membrane. Although state of the art, various forms of the foregoing technique prove largely unreliable due to difficulties not only in handling the membrane but also of preparing the membrane prior to handling.

Accordingly, it would be highly desirable to provide a new and improved method of preparing a specimen for TEM study or examination.

It is a purpose of the present invention to provide a new and improved method of preparing a specimen for TEM study or examination that is easy to carry out with existing TEM technology.

It is another purpose of the present invention to provide a new and improved method of preparing a specimen for TEM study or examination that is efficient and inexpensive.

It is still another provision of the present invention to accommodate the long-felt need of providing successful membrane formation and manipulation for TEM study or examination.

It is a further purpose of the present invention to provide a new and improved method of preparing a specimen for TEM study or examination that is very reliable.

It is still a further purpose of the present invention to provide a new and improved method of preparing a specimen for TEM study or examination that eliminates substantially the possibility of damaging a sample during sample preparation operations.

SUMMARY OF THE INVENTION

The above problems and others are at least partially solved and the above purposes and others are realized in exemplary embodiments of improved methods of examining a specimen and of preparing a specimen for examination or study. In a specific embodiment, provided is a method of examining a specimen comprising the steps of providing transmission electron microscope apparatus, mounting a specimen in a vacuum chamber of focused ion beam apparatus, isolating a site of the specimen with the focused ion beam apparatus in the vacuum chamber, and with the site located in the vacuum chamber, examining the site with the transmission electron microscope apparatus. In the present embodiment, the step of isolating the site of the specimen with the focused ion beam apparatus may further include the steps of identifying the site, actuating the focused ion beam apparatus to generate a focused ion beam, and selectively directing the focused ion beam toward the specimen to mill a membrane containing the site and sever the membrane from the specimen.

The present method may further include the step of removing the site from the specimen which may include providing micro-manipulator apparatus housed in the vacuum chamber, the micro-manipulator apparatus having an engagement element, and selectively actuating the micro-manipulator apparatus to move the engagement element to engage, carry and remove the membrane from the specimen.

Examination of the site with the transmission electron microscope apparatus may further include positioning the membrane in line with the transmission electron microscope apparatus, and actuating the transmission electron microscope apparatus. Furthermore, positioning the membrane in line with the transmission electron microscope apparatus may further include the step of selectively actuating the micro-manipulator apparatus to move the engagement element to either hold the membrane in line with the transmission electron microscope apparatus or place the membrane against a support grid located in line with the transmission electron microscope apparatus.

BRIEF DESCRIPTION OF THE DRAWINGS

The foregoing and further and more specific objects and advantages of the instant invention will become readily apparent to those skilled in the art from the following detailed description thereof taken in conjunction with the drawings in which.

DETAILED DESCRIPTION OF PREFERRED EMBODIMENTS

Figure 1:
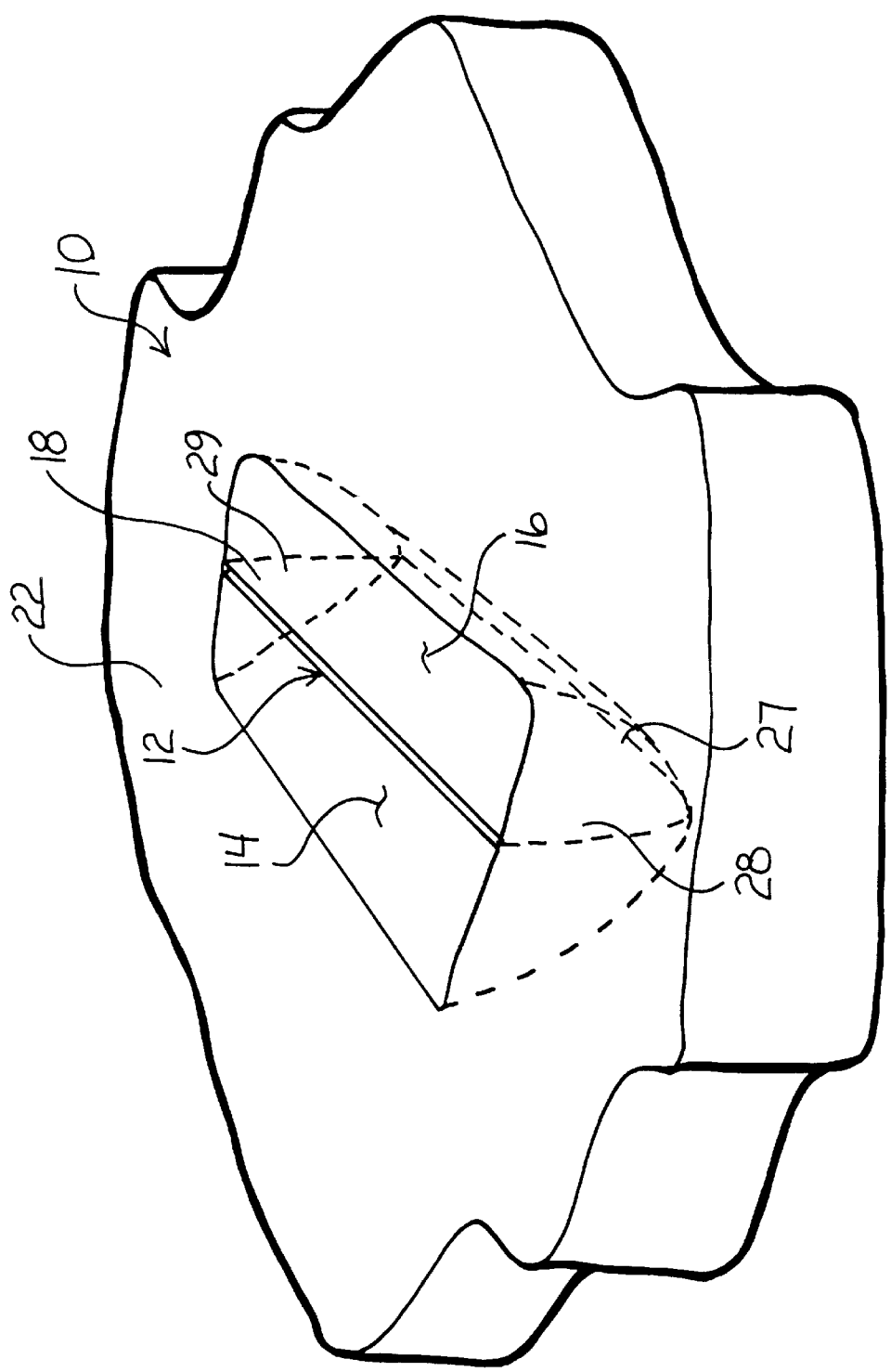
FIG. 1 illustrates a fragmented isometric view of a specimen having trenches formed therein bounding a blank containing a site desired for study or examination.

The present invention provides, among other things, new and improved methods of examining a sample and of preparing a specimen for transmission electron microscopic (TEM) apparatus study and/or examination. In general, preferred embodiments of the present invention generally include the steps of preparing a site of a specimen for TEM apparatus examination, removing the site from the specimen, mounting the specimen against a support grid and actuating TEM apparatus for imaging the site.

In TEM apparatus, an electron beam is normally directed against an object or sample of a specimen to be magnified. Some of the electrons either absorb into or bounce off of the sample, while others pass through the sample to form a magnified image of the sample. For exemplary results, a sample of the specimen must be cut very thin, such as no more than a few thousand angstroms thick, to be observed and used in TEM apparatus. A photographic plate or fluorescent screen is normally placed beyond the sample to record the magnified image. As a matter of interest, TEM apparatus are capable of magnifying an object up to one million times.

For the purposes of orientation, all electron microscopes include several basic elements including, among other things, an electron gun that emits electrons that strike the sample to create a magnified image. Magnetic "lenses" that generate magnetic fields are used to direct and focus the electrons because conventional lenses used in optical microscopes to focus visible light do not work with electrons. Because electrons are easily scattered by air molecules, the interior of a TEM APPARATUS must contain a very high vacuum. Finally, electron microscopes also have a system that records or displays the image produced by the electrons.

As previously mentioned, a sample of a specimen desired to be examined by TEM apparatus must be cut very thin to be imaged by TEM apparatus. Depending on the nature of the specimen, fabricating such thin samples normally requires a variety of thinning techniques. For instance, cross sections of continuous thin film samples for TEM apparatus analysis can be prepared by precision mechanical polishing and ion-beam milling using a broad beam of accelerated ions provided, for instance, from conventional focused ion beam (FIB) apparatus. Conventional FIB apparatus may be used for preparing samples both in plan-view and cross-sectional configurations. Focused ion beam apparatus may further be employed for high spatial resolution material removal and deposition applications for integrated circuit repair and circuit modification, and for preparation of site-specific or material-specific sample preparation in semiconductor, data-storage and other industry applications.

Specimen preparation using FIB apparatus may normally involve a pre-thinning stage in which a thin slice of a specimen, i.e., 30–60 μm wide×3 mm long, is prepared by mechanical polishing followed by the subsequent removal of additional localized material to create a thin membrane comprising, for instance, a cross section of the specimen. The thin membrane may then be imaged with TEM apparatus.

Turning now to the drawings, in which like reference characters indicate corresponding elements throughout the several views, attention is first directed to FIG. 1 illustrating a perspective view of a specimen generally designated by the reference character 10. Consistent with the preceding discussion, specimen 10 may be provided as a semiconductor or other selected subject desired to be examined by TEM apparatus.

Figure 1A:
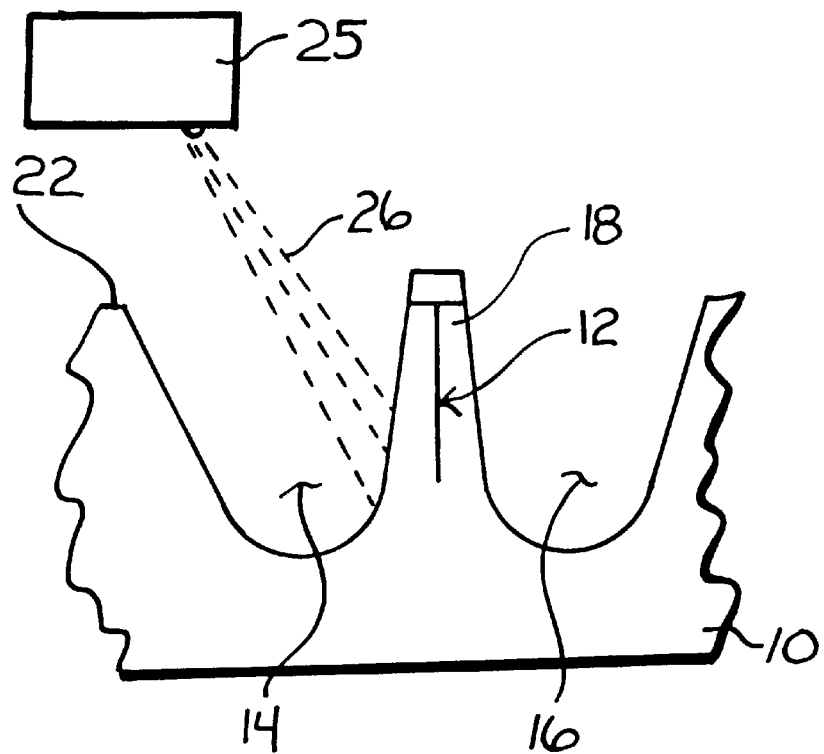
FIG. 1A illustrates a vertical sectional view of the specimen of FIG. 1 showing the trenches as they would appear having been formed on either side of a blank in a task carried out in accordance with a specific method embodiment.

In accordance with preferred methods of examining a specimen and of preparing a specimen for TEM apparatus examination, the present invention may first begin with tasks of providing a specimen 10 and identifying a specific site 12 of specimen 10 desired to be examined. For the purposes of the present discussion, site 12 may comprise a localized generally transverse cross section of specimen 10. Upon selection of site 12, the method further includes a task of isolating site 12 by, for instance, forming trenches 14 and 16 into specimen 10 on either side of site 12 to form a blank 18 containing site 12, of which may also be seen in FIG. 1A illustrating a vertical sectional view of specimen 10. Trenches 14 and 16 are normally formed of a depth sufficient to contain site 12 in blank 18.

In a specific embodiment, formation of trenches 14 and 16 may first include a task of depositing a protective layer onto a surface 22 of specimen 10 locally adjacent site 12. Comprised preferably of a high atomic number metal such as tungsten, platinum other similar material, the protective layer protects surface 22 of specimen 10 at site 12 from eroding during the formation of trenches 14 and 16. In this regard, once the protective layer is deposited upon surface 22 at or otherwise adjacent site 12, a task may then be performed to remove specimen 10 material on opposing sides of site 12 by milling the specimen 10 material away with, for instance, a focused ion beam 25 generated from FIB apparatus 26 shown generally in FIG. 1A. During the milling process, the protective layer substantially impedes erosion of site 12 due to sputtering by, for instance, FIB tail/extension that normally occurs during FIB milling processes. If damage to the entire surface 22 of specimen is of a concern to the user, the protective layer may be vapor- or sputter-deposited over the entire surface 22 if so desired.

As evinced in FIG. 1, a lower end 27 and opposing side edges 28 and 29 of blank 18 remain integral with specimen 10 after formation of trenches 14 and 16. To further isolate site 12 for subsequent study or examination, the present invention further includes a task of severing or detaching the lower end of blank 18 from specimen 10. Severing the lower end of blank 18 may be carried out in, for instance, at least two different ways, neither of which is intended to be limiting but merely illustrative of how the lower end of blank 18 may be severed or detached from specimen 10.

Figure 2:
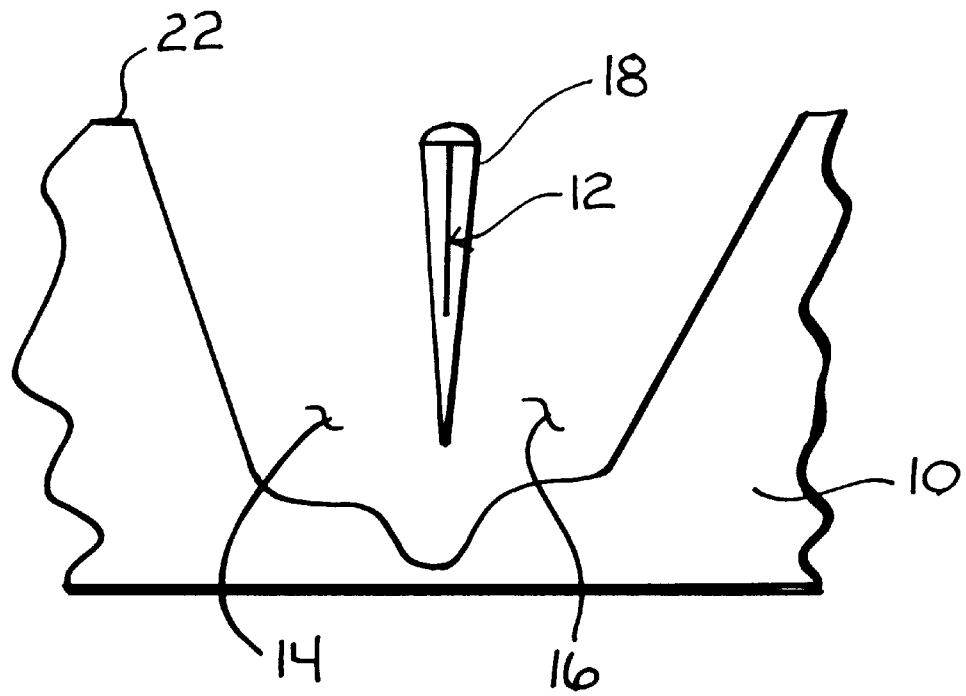
FIG. 2 illustrates a vertical sectional view of the specimen of FIG. 1 further showing a blank having been partially severed from the specimen in a task carried out in accordance with a specific method embodiment.
Figure 3:
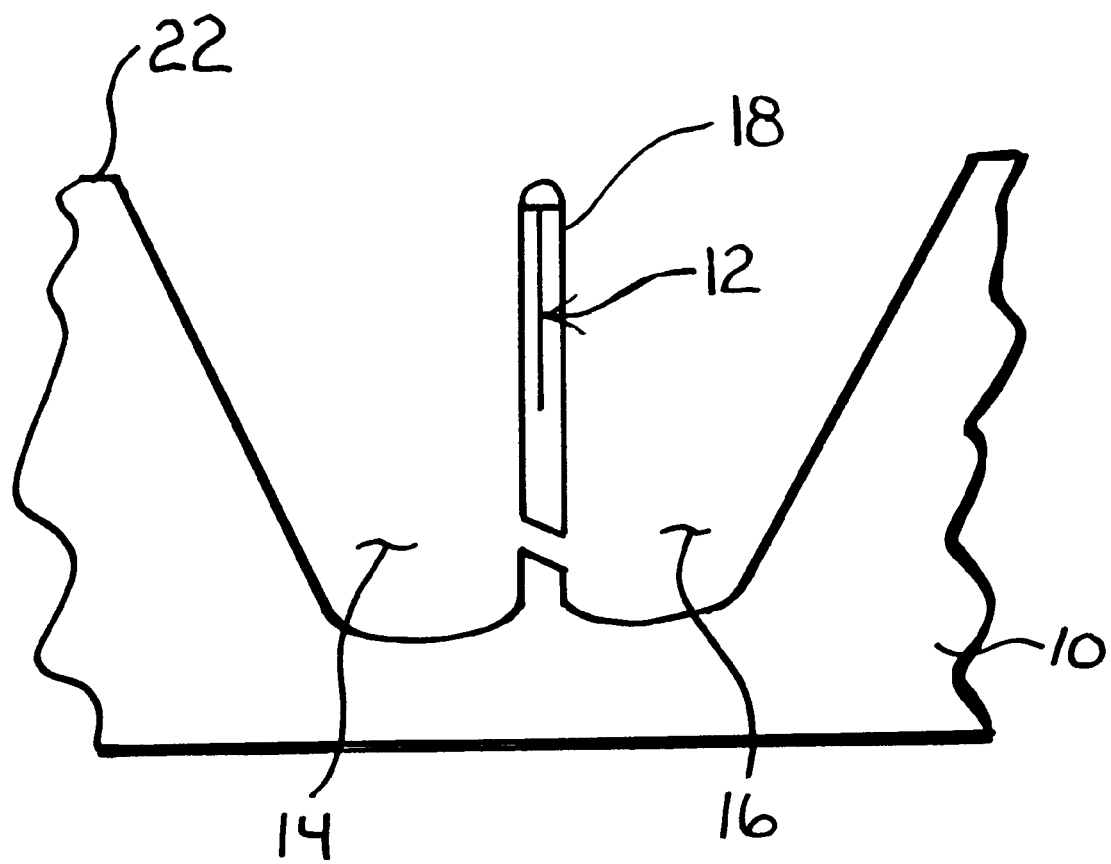
FIG. 3 illustrates a vertical sectional view of the specimen of FIG. 1 further showing a blank having been partially severed from the specimen in a task carried out in accordance with another method embodiment.

In a specific example, specimen 10 may be tilted to an angle sufficient to allow a user to view blank 18 and to mechanically sever (as seen in FIG. 3) the lower end of blank 18 using FIB apparatus or other similar and suitable mechanical cutting apparatus or technique. Regarding FIG. 2, a user may alternatively tilt specimen 10 to an angle sufficient to allow a user to mill, such as with FIB apparatus, portions of trenches 14 and 16 in line with the lower end of blank 18 to undercut the lower end of blank 18 away from specimen 10.

Figure 4:
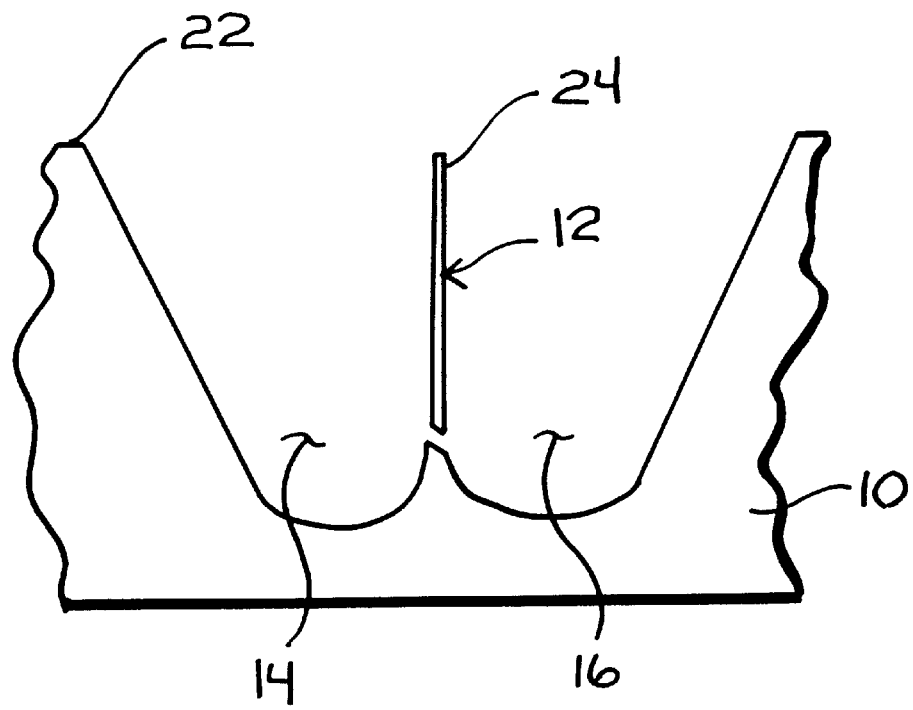
FIG. 4 illustrates a vertical sectional view very similar to the views of FIG. 2 and FIG. 3, further showing a membrane having been formed from a blank in a task carried out in accordance with a specific method embodiment.
Figure 5:
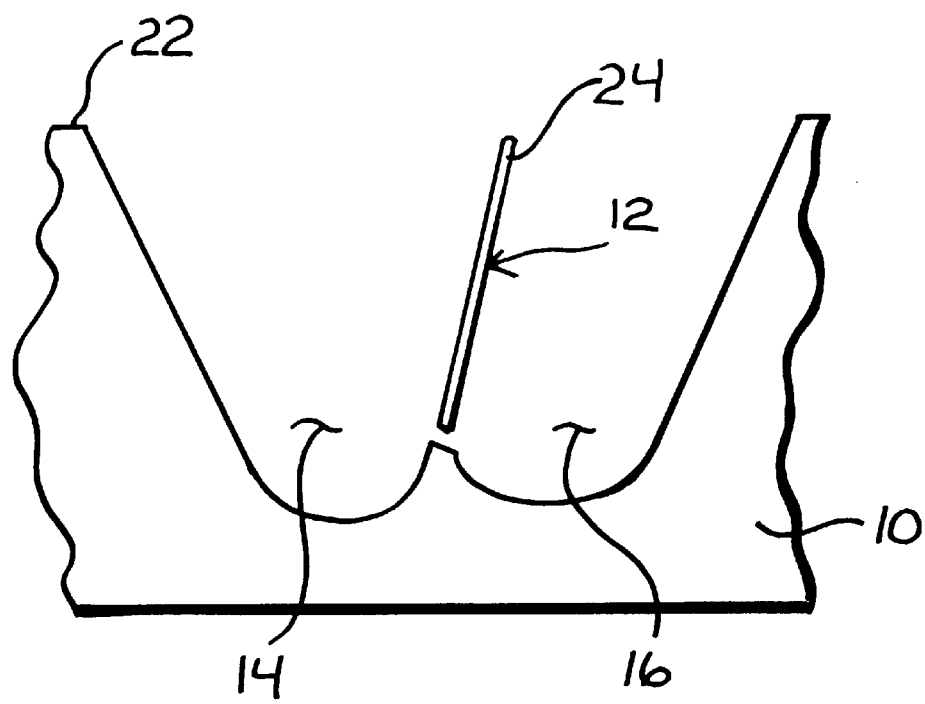
FIG. 5 illustrates a vertical sectional view of the specimen of FIG. 1 further showing the membrane of FIG. 4A as it would appear having been completely detached from the specimen in a task carried out in accordance with a specific method embodiment.
Figure 4A:
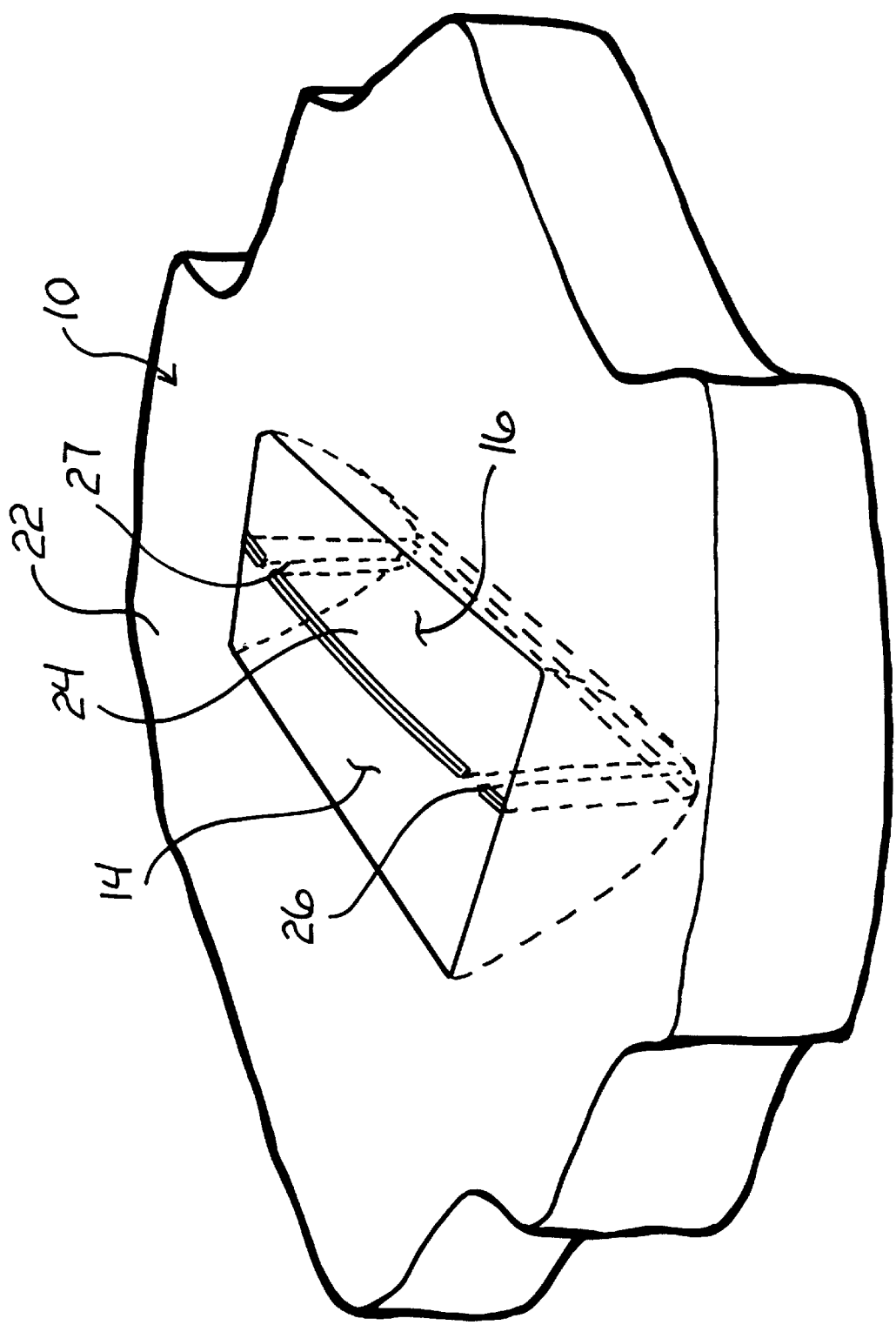
FIG. 4A illustrates a perspective view of the specimen of FIG. 1 further showing the membrane of FIG. 4 as it would appear having been completely detached from the specimen in a task carried out in accordance with a specific method embodiment.

Upon detachment of the lower end of blank 18 from specimen 10, the present invention further includes a task of thinning blank 18 to form a membrane 24 (FIG. 4) isolating or otherwise containing site 12. Thinning blank 18 may be carried out by removing localized excess specimen 10 material from blank 18 by milling excess blank material away using FIB apparatus. After forming membrane 24, membrane 24 may be completely detached from specimen 10 by severing each side of membrane 24 (FIG. 4A) at 26 and 27 from specimen 10 with, for instance, FIB apparatus. The complete detachment of membrane 24 from specimen 10 may also be seen clearly in FIG. 5.

Figure 6:
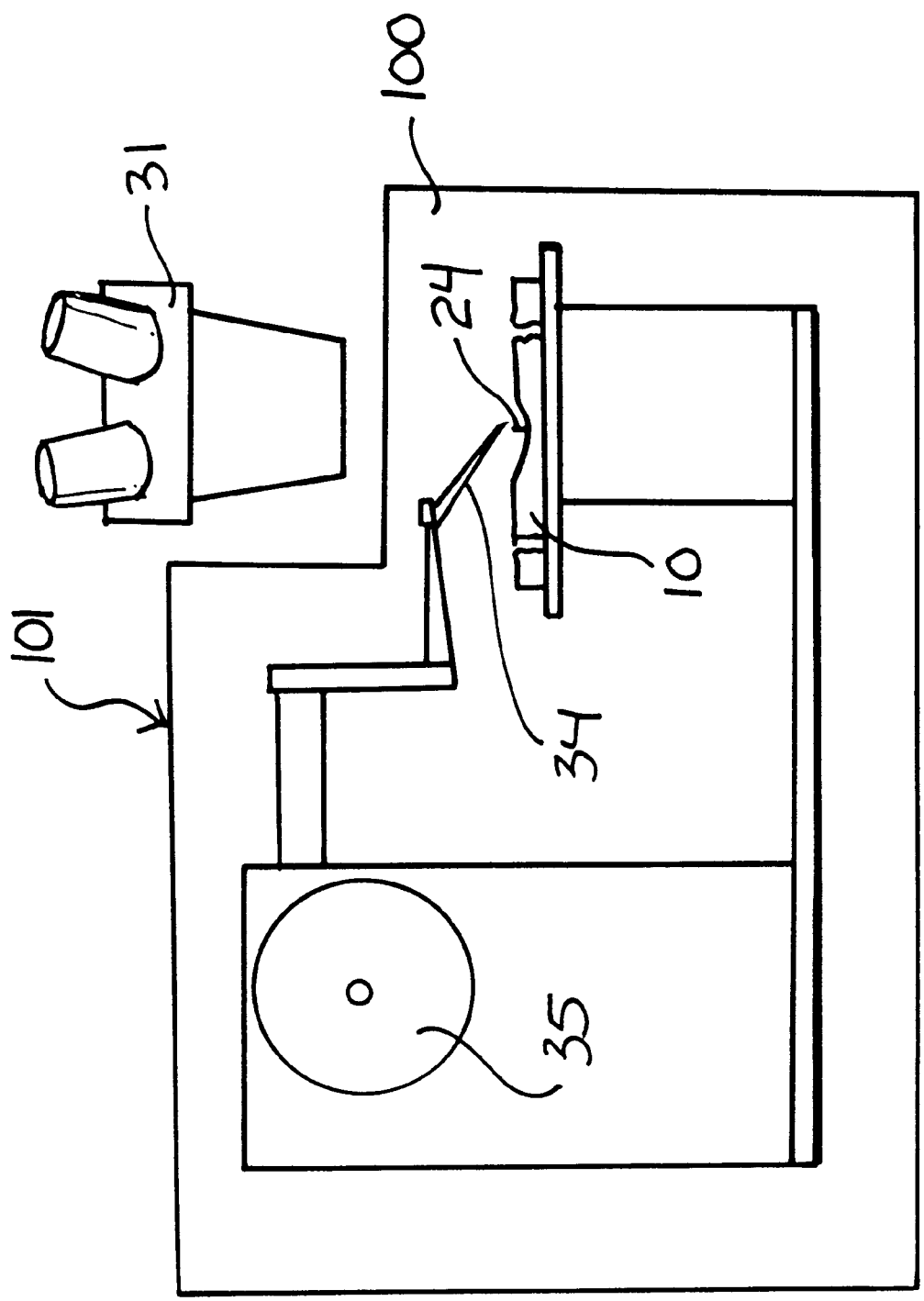
FIG. 6 is a schematic representation of a manipulator apparatus shown as it would appear removing the completely detached membrane of FIG. 5 from the specimen and placing the membrane onto a support film in tasks carried out in accordance with a specific method embodiment.
Figure 7:
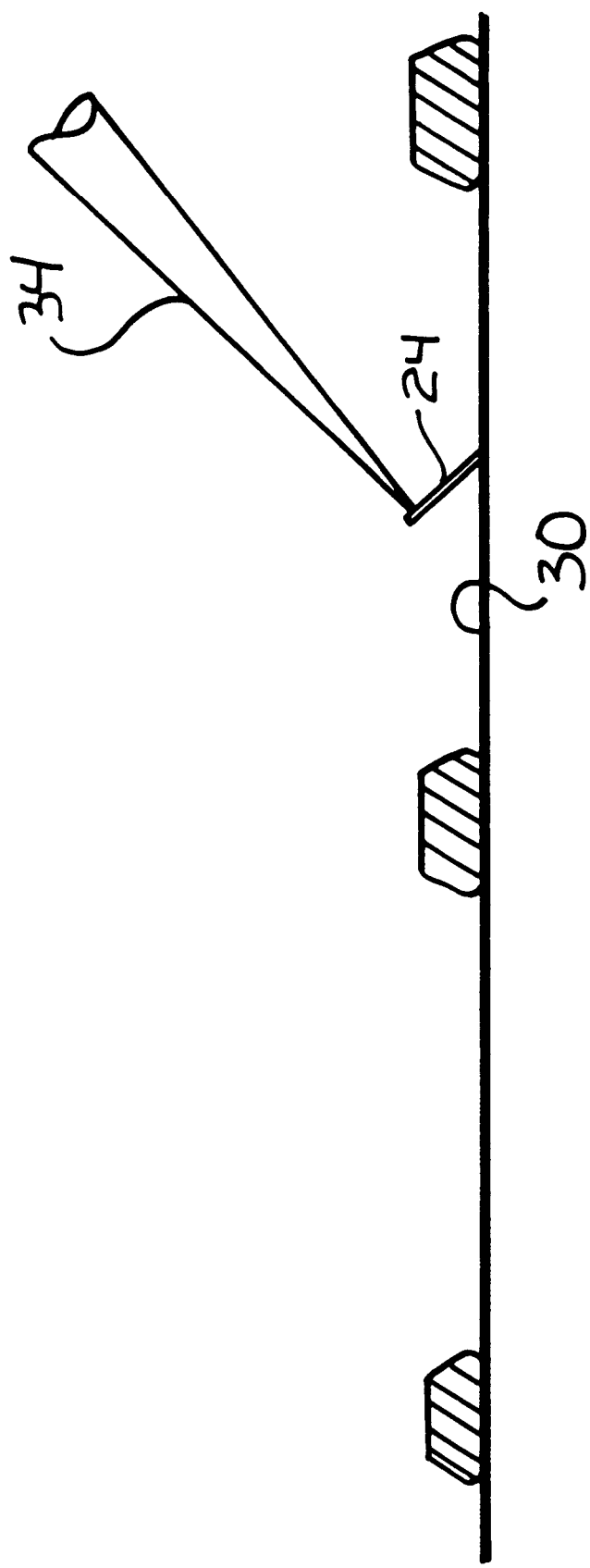
FIG. 7 is an enlarged fragmented perspective view of the probe of FIG. 6 shown as it would appear placing the membrane onto a support film in a task carried out in accordance with a specific method embodiment.

Regarding FIG. 6, detachment of membrane 24 from specimen 10 is followed by tasks of removing membrane 24 from specimen 10 and transferring to and depositing membrane 24 against a conventional support film or grid 30 in line with TEM apparatus 31 for study or examination generally by actuating TEM apparatus 31 and 30 is shown only in FIG. 7. Support grid 30 is preferably an electron-transparent support fixture suitable for use in supporting a sample for TEM apparatus study or examination. To manipulate or otherwise remove membrane 24 from specimen 10 and transfer it to support grid 30 may be carried out by providing an engagement element or probe 34 mounted to or otherwise carried by micro-manipulator apparatus 35 and actuating micro-manipulator apparatus 35 selectively for moving probe 34. Micro-manipulator apparatus 35 is of a conventional sort operative for controlling probe 34 with sub-micron precision in the x, y, and z directions, further details of which will not be further discussed as they will readily occur to the skilled artisan.

With continuing reference to FIG. 6, micro-manipulator apparatus 35 may be actuating for moving probe 34 to engage and couple probe 34 with membrane 24, lift membrane 24 away from specimen 10 and transfer membrane 24 against support grid 30 as shown in FIG. 7. Upon engagement of probe 34 with membrane 24, attractive forces, due primarily to electrostatic and capillary forces, between probe 34 and membrane 24 occasion membrane 24 to adhere to probe 34 allowing a user to then lift membrane 24 away from specimen 10 by selective actuation of micro-manipulator apparatus 35. With membrane 24 attached to probe 34, probe 34 may then be moved adjacent support film 30 and membrane 24 placed against support film 30 where it sticks and releases from probe 34. Although not shown, support grid 30 may be coated with a support film if desired in accordance with conventional practice.

Although the two primary attractive forces between probe 34 and membrane 24 sufficient to cause membrane 24 to adhere to probe 34 are electrostatic and capillary forces, water absorbed onto the surface of probe 34 and membrane 24 can alone cause membrane 24 to adhere to probe 34 in the foregoing operation of removing membrane 24 from specimen 10 if performed in ambient conditions. In this regard, the task of lifting membrane 24 from specimen 10 and mounting membrane 24 against support film 30 can alternately be carried out under high humidity conditions using a blunt, large tip radius probe. Nevertheless, once extracted from specimen 10 and positioned against support grid 30 in the foregoing exemplary manner, imaging of membrane 24 may be carried out generally by actuating TEM apparatus 31 of FIG. 6 in a task as initiated above.

In an alternate and exemplary embodiment of the present invention, and with continuing reference to FIG. 6, micro-manipulator 34, probe 34 and specimen 10 may be housed, mounted in or contained in an FIB instrument chamber 100 of FIB apparatus 101 for allowing the foregoing method steps of the present invention to be carried out directly inside FIB instrument chamber 100 under vacuum contained by FIB instrument chamber 100. In this regard, performing the foregoing method directly in FIB instrument chamber 100 permits necessary micro-manipulation of membrane 24 to be visually monitored using either the imaging capability of FIB apparatus 101 and perhaps an in-chamber optical light microscope/camera thereby providing a better depth of focus and higher degree of control during the manipulation process.

With specimen 10 contained within FIB instrument chamber 100 throughout the duration of the above-described method steps, micro-manipulation of membrane 24 may be performed in-situ using micro-manipulator apparatus 35 in-chamber under vacuum conditions thus eliminating substantially exposure of membrane 24 to ambient conditions. In this embodiment of the present invention, exposure of membrane 24 to ambient conditions is substantially eliminated which inhibits the occurrence of surface particulate or residual contamination on membrane 24 that can otherwise compromise imaging of membrane 24. Furthermore, necessary micro-manipulation of membrane 24 of with micro-manipulator apparatus 35 and probe 34 may be suitably accomplished by selectively controlling the attachment and detachment of membrane 24 to and from probe 34 using one or more suitable adhesion mechanisms applied directly to probe 34. Suitable adhesion mechanisms sufficient to carry out the desired function of controlling the attachment and detachment of membrane 24 from probe 34 may include at least one of controlled and predetermined pre-charged or induced electrostatic forces introduced to probe 34, a pre-applied coating or an in-situ-dispensed amount of a suitable adhesive mechanism or system of adhesives added directly to probe 34, and an in-situ deposited bonding medium added directly to probe 34 and/or to a supporting fixture for supporting membrane 24 for TEM apparatus imaging. In this regard, the attachment and detachment of membrane 24 to and from probe 34 may be controlled by employing and regulating one or more of the foregoing adhesion mechanisms.

Figure 8:
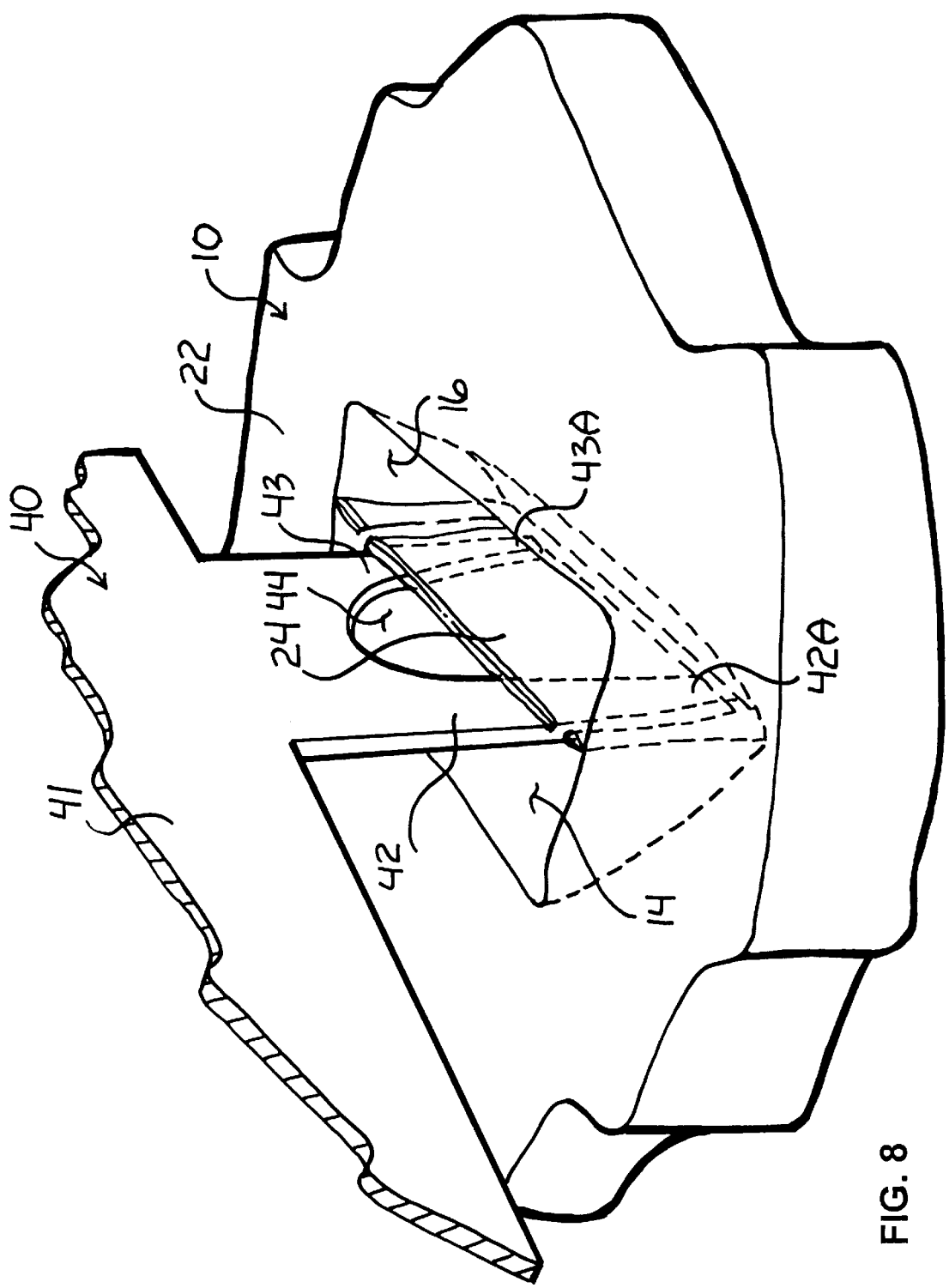
FIG. 8 illustrates a support fixture shown as it would appear removing the membrane of FIG. 5 from the specimen in a task carried out in accordance with a specific method embodiment.

In another embodiment of the present method, probe 34 may be replaced with an alternate engagement element comprising a support fixture 40 for supporting membrane 24 for TEM apparatus imaging. Referring to FIG. 8 illustrating support fixture 40 as it would appear removing membrane 24 from specimen 10, support fixture 40 may be mounted with micro-manipulator apparatus 35 and, through actuation of micro-manipulator apparatus 35, selectively manipulated to remove membrane 24 from sample 10.

Figure 9:
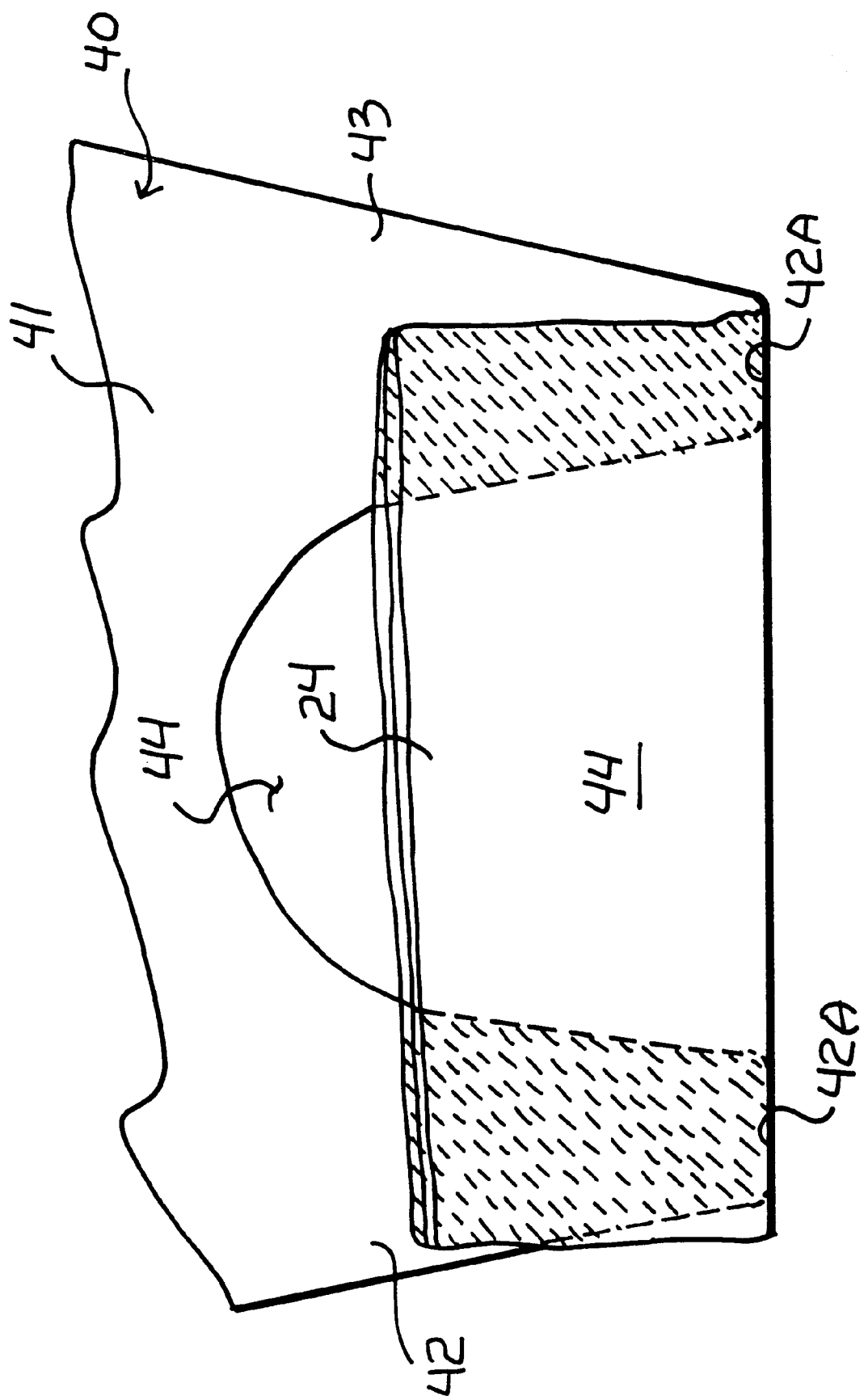
FIG. 9 illustrates a front elevational view of the support fixture of FIG. 8 shown as it would appear holding the membrane.

In a specific example, support fixture 40 includes body 41 having a pair of spaced-apart tines 42 and 43 extending outwardly therefrom each terminating with an outer end 42A and 42B, respectively. Support fixture 40 may be manipulated adjacent membrane 24 after formation thereof. With tines 42 and 43 supplied with a suitable and controlled adhesion mechanism such as at least one of a controlled and predetermined pre-charged or induced electrostatic forces added directly to tines 42 and 43, a pre-determined and pre-applied coating of an in-situ-dispensed amount of a suitable adhesive mechanism or system of adhesives added directly to tines 42 and 43 and an in-situ deposited bonding medium added directly to tines 42 and 43, membrane 24 will adhere to tines 42 and 43 when engaged thereagainst. In a preferred manner of engagement, tines 42 and 43 may be engaged to membrane 24 with membrane 24 to desirably and substantially traverse tines 42 and 43 and a gap 44 formed or otherwise defined intermediate tines 42 and 43 as shown substantially in FIG. 9. With membrane 24 so carried by support fixture, tasks may be carried out to move support fixture 40, such as by actuation of micro-manipulator apparatus 35, to position tines 42 and 43 adjacent TEM apparatus 31 for analysis of portions membrane 24 residing in gap 44. As a result, unobstructed TEM apparatus imaging of portions of membrane 24 intermediate tines 42 and 43 at gap 44 may be easily carried out in a task generally upon actuation of TEM apparatus 31.

The present invention has been described above with reference to a preferred embodiment. However, those skilled in the art will recognize that changes and modifications may be made in the described embodiments without departing from the nature and scope of the present invention. Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. An examination method comprising the steps of:
   locating a specimen and a holder in a substantial vacuum, the holder having tines separated by a gap;
   forming a membrane of the specimen with focused ion beam apparatus;
   moving the holder toward the membrane until the tines engage and adhere to the membrane with at least part of the membrane spanning the gap between the tines;
   moving the holder to move the membrane away from the specimen and to a position in line with transmission electron microscope apparatus; and
   examining the part of the membrane substantially along the gap with the transmission electron microscope apparatus.

2. The method of claim 1, wherein the step of forming a membrane further includes the steps of:
   generating a focused ion beam with the focused ion beam apparatus; and
   milling the membrane from the specimen with the focused ion beam.

3. An examination method comprising the steps of:
   locating a membrane and a holder in a substantial vacuum, the holder having tines separated by a gap;
   moving the holder toward the membrane until the tines engage and adhere to the membrane with at least part of the membrane spanning the gap between the tines;
   moving the holder to move the membrane to a position in line with transmission electron microscope apparatus; and
   examining the part of the membrane located substantially along the gap with the transmission electron microscope apparatus.

4. A method of preparing a specimen for transmission electron microscope examination comprising the steps of:
   locating a specimen and a holder in a substantial vacuum, the holder having tines separated by a gap;
   forming a membrane of the specimen with focused ion beam apparatus;
   moving the holder toward the membrane until the tines engage and adhere to the membrane with at least part of the membrane spanning the gap between the tines; and
   moving the holder to move the membrane away from the specimen and to locate the part of the membrane extending along the gap at a position in line with transmission electron microscope apparatus.

5. The method of claim 4, wherein the step of forming a membrane further includes the steps of:
   generating a focused ion beam with the focused ion beam apparatus; and
   milling the membrane from the specimen with the focused ion beam.

6. A method of preparing a specimen for transmission electron microscope examination comprising the steps of:
   locating a membrane and a holder in a substantial vacuum, the holder having tines separated by a gap;
   moving the holder toward the membrane until the tines engage and adhere to the membrane with at least part of the membrane spanning the gap between the tines; and
   moving the holder to locate the part of the membrane along the gap at a position in line with transmission electron microscope apparatus.

7. An examination method comprising the steps of:
   locating a specimen and a holder in a substantial vacuum, the holder including a controlled adhesion mechanism;
   forming a membrane of the specimen with focused ion beam apparatus;
   moving the holder toward the membrane until the holder engages and adheres to the membrane, the controlled adhesion mechanism for providing a controlled adhesion between the holder and the membrane;
   moving the holder to move the membrane away from the specimen and to a position in line with transmission electron microscope apparatus; and
   with the membrane held by the holder, examining the membrane with the transmission electron microscope apparatus.

8. The method of claim 7, wherein the step of forming a membrane further includes the steps of:
   generating a focused ion beam with the focused ion beam apparatus; and
   milling the membrane from the specimen with the focused ion beam.

9. The method of claim 7, wherein the controlled adhesion mechanism comprises at least one of a controlled electrostatic force, an adhesive and a bonding medium.

10. An examination method comprising the steps of:
    locating a membrane and a holder in a substantial vacuum, the holder including a controlled adhesion mechanism;
    moving the holder toward the membrane until the holder engages and adheres to the membrane, the controlled adhesion mechanism for providing a controlled adhesion between the holder and the membrane;
    moving the holder to move the membrane to a position in line with transmission electron microscope apparatus; and
    with the membrane held by the holder, examining the membrane with the transmission electron microscope apparatus.

11. The method of claim 10, wherein the controlled adhesion mechanism comprises at least one of a controlled electrostatic force, an adhesive and a bonding medium.

12. A method of preparing a specimen for transmission electron microscope examination comprising the steps of:

locating a specimen and a holder in a substantial vacuum, the holder including a controlled adhesion mechanism;

forming a membrane of the specimen with focused ion beam apparatus;

moving the holder toward the membrane until the holder engages and adheres to the membrane, the controlled adhesion mechanism for providing a controlled adhesion between the holder and the membrane; and moving the holder to move the membrane away from the specimen and to a position in line with transmission electron microscope apparatus.

13. The method of claim 12, wherein the step of forming a membrane further includes the steps of:

generating a focused ion beam with the focused ion beam apparatus; and milling the membrane from the specimen with the focused ion beam.

14. The method of claim 12, wherein the controlled adhesion mechanism comprises at least one of a controlled electrostatic force, an adhesive and a bonding medium.

15. A method of preparing a specimen for transmission electron microscope examination comprising the steps of:

locating a membrane and a holder in a substantial vacuum, the holder including a controlled adhesion mechanism;

moving the holder toward the membrane until the holder engages and adheres to the membrane, the controlled adhesion mechanism for providing a controlled adhesion between the holder and the membrane; and moving the holder to move the membrane to a position in line with transmission electron microscope apparatus.

16. The method of claim 15, wherein the controlled adhesion mechanism comprises at least one of a controlled electrostatic force, an adhesive and a bonding medium.

* * * * *

UNITED STATES PATENT AND TRADEMARK OFFICE
CERTIFICATE OF CORRECTION

PATENT NO.   : 6,188,068 B1　　　　　　　　　　　　　　　　　　　　　Page 1 of 1
DATED        : February 13, 2001
INVENTOR(S)  : Frederick F. Shaapur, Roger J. Graham It is certified that error appears in the above-identified patent and that said Letters Patent is hereby corrected as shown below:

Title page,
Replace "METHODS OF EXAMINING A SPECIMEN AND OF PREPARING A SPECIMEN FOR TRANSMISSION MICROSCOPIC EXAMINATION" with -- METHODS OF EXAMINING A SPECIMEN AND OF PREPARING A SPECIMEN FOR TRANSMISSION ELECTRON MICROSCOPIC EXAMINATION --.

Signed and Sealed this

Nineteenth Day of February, 2002

*Attest:*

JAMES E. ROGAN
*Attesting Officer*　　　*Director of the United States Patent and Trademark Office*